United States Patent
Rapoport (10) Patent No.: US 10,174,569 B2
(45) Date of Patent: Jan. 8, 2019

(54) NMR/MRI-BASED INTEGRATED SYSTEM FOR ANALYZING AND TREATING OF A DRILLING MUD FOR DRILLING MUD RECYCLING PROCESS AND METHODS THEREOF

(71) Applicant: Aspect International (2015) Private Limited, Singapore (SG)

(72) Inventor: Uri Rapoport, Moshav Ben Shemen (IL)

(73) Assignee: Aspect International (2015) Private Limited, Singapore (SG)

( * ) Notice: Subject to any disclaimer, the term of this patent is extended or adjusted under 35 U.S.C. 154(b) by 158 days.

(21) Appl. No.: 14/899,645

(22) PCT Filed: Jun. 16, 2014

(86) PCT No.: PCT/IL2014/050544
§ 371 (c)(1),
(2) Date: Dec. 18, 2015

(87) PCT Pub. No.: WO2014/203245
PCT Pub. Date: Dec. 24, 2014

(65) Prior Publication Data
US 2016/0230482 A1  Aug. 11, 2016

Related U.S. Application Data (60) Provisional application No. 61/837,205, filed on Jun. 20, 2013, provisional application No. 61/889,113, filed on Oct. 10, 2013.

(51) Int. Cl.
*E21B 21/06* (2006.01)
*G05B 13/04* (2006.01)
(Continued)

(52) U.S. Cl.
CPC ........... *E21B 21/06* (2013.01); *G01N 24/081* (2013.01); *G01N 33/2823* (2013.01); *G05B 13/042* (2013.01); *G01V 3/32* (2013.01)

(58) Field of Classification Search
CPC .............................. E21B 21/06; G01N 24/081
See application file for complete search history.

(56) References Cited

U.S. PATENT DOCUMENTS

| | | | |
|---|---|---|---|
| 2,768,529 A | 10/1956 | Hagler, Sr. | |
| 3,175,403 A | 3/1965 | Nelson | |

(Continued)

FOREIGN PATENT DOCUMENTS

| | | |
|---|---|---|
| CN | 1236478 | 11/1999 |
| CN | 1291873 | 4/2001 |

(Continued)

OTHER PUBLICATIONS

Gunnerod et al., "Highly automated drilling fluids system improves HSE and efficiency, reduces personnel needs", Drilling Contractor, Feb. 2009, 4 pages.*

(Continued)

*Primary Examiner* — Whitney Moore
(74) *Attorney, Agent, or Firm* — Pearl Cohen Zedek Latzer Baratz LLP (57) ABSTRACT

An NMR/MRI-based integrated system for analyzing and treating of a drilling mud for drilling mud recycling line; the system comprising drilling mud recycling equipment; an NMR/MRI device configured to provide at least one image of at least a portion of the drilling mud at least one characterized recycling step in the drilling mud recycling line; and a processor for analyzing and controlling the recycling of the drilling mud; wherein the NMR/MRI-based integrated system is operating in a method of analyzing the NMR/MRI image online; operatively communicating results (Continued)

of the analysis to the drilling mud recycling equipment; and online feedback controlling at least one step in the recycling of the drilling mud recycling equipment, thereby controlling automatically at least one step in the recycling of the drilling mud recycling.

19 Claims, 2 Drawing Sheets

(51) Int. Cl.
  *G01N 24/08* (2006.01)
  *G01N 33/28* (2006.01)
  *G01V 3/32* (2006.01)

(56) References Cited

U.S. PATENT DOCUMENTS

| | | | |
|---|---|---|---|
| 3,989,630 A | 11/1976 | Walker |
| 4,417,474 A | 11/1983 | Elderton |
| 4,468,622 A | 8/1984 | Frese et al. |
| 4,697,594 A | 10/1987 | Mayo, Jr. |
| 4,904,603 A | 2/1990 | Jones et al. |
| 4,994,746 A | 2/1991 | Panosh |
| 5,023,551 A | 6/1991 | Kleinberg et al. |
| 5,145,189 A | 9/1992 | Pope |
| 5,161,409 A | 11/1992 | Hughes et al. |
| 5,168,226 A | 12/1992 | Hinks |
| 5,208,534 A | 5/1993 | Okamoto et al. |
| 5,280,243 A | 1/1994 | Miller |
| 5,306,909 A | 4/1994 | Jones et al. |
| 5,479,925 A | 1/1996 | Dumoulin et al. |
| 5,532,593 A | 7/1996 | Maneval et al. |
| 5,557,103 A | 9/1996 | Hughes et al. |
| 5,557,201 A | 9/1996 | Kleinberg et al. |
| 5,696,448 A | 12/1997 | Coates et al. |
| 5,705,927 A | 1/1998 | Sezginer et al. |
| 5,757,187 A | 5/1998 | Wollin |
| 5,784,333 A | 7/1998 | Tang et al. |
| 5,986,454 A | 11/1999 | Leifer |
| 6,090,728 A | 7/2000 | Yenni, Jr. et al. |
| 6,107,796 A | 8/2000 | Prammer |
| 6,178,807 B1 | 1/2001 | Baldwin et al. |
| 6,215,304 B1 | 4/2001 | Slade |
| 6,268,726 B1 | 7/2001 | Prammer et al. |
| 6,362,619 B2 | 3/2002 | Prammer et al. |
| 6,412,337 B1 | 7/2002 | Arzate et al. |
| 6,421,337 B1 | 7/2002 | Rao et al. |
| 6,452,390 B1 | 9/2002 | Wollin |
| 6,507,191 B1 | 1/2003 | Eguchi et al. |
| 6,518,758 B1 | 2/2003 | Speier et al. |
| 6,549,007 B1 | 4/2003 | Hills et al. |
| 6,550,327 B1 | 4/2003 | Van Berk |
| 6,646,437 B1 | 11/2003 | Chitale et al. |
| 6,807,857 B2 | 10/2004 | Storm, Jr. et al. |
| 6,856,132 B2 | 2/2005 | Appel et al. |
| 6,907,375 B2 | 6/2005 | Guggari et al. |
| 6,913,827 B2 | 7/2005 | George et al. |
| 6,952,096 B2 | 10/2005 | Freedman |
| 7,075,366 B2 | 7/2006 | Deem et al. |
| 7,295,933 B2 | 11/2007 | Gysling et al. |
| 7,352,179 B2 | 4/2008 | Chen et al. |
| 7,486,071 B2 | 2/2009 | Care et al. |
| 7,489,132 B2 | 2/2009 | Arik et al. |
| 7,570,058 B1 | 8/2009 | Wong et al. |
| 7,823,656 B1 | 11/2010 | Williams |
| 7,908,034 B2 | 3/2011 | Gray |
| 7,921,731 B2 | 4/2011 | Bajikar et al. |
| 8,024,962 B2 | 9/2011 | Tonmukayakul et al. |
| 8,143,887 B2 | 3/2012 | Pusiol |
| 8,256,532 B2 | 9/2012 | Gray |
| 8,373,412 B2 | 2/2013 | Kruspe et al. |
| 8,461,842 B2 | 6/2013 | Thuringer et al. |
| 8,469,118 B2 | 6/2013 | Passade-Boupat et al. |
| 8,736,263 B2 | 5/2014 | Minh |
| 8,763,170 B1 | 7/2014 | Ungarsohn |
| 8,763,710 B2 | 7/2014 | Graue |
| 8,791,695 B2 | 7/2014 | Balcom et al. |
| 8,807,084 B2 | 8/2014 | Rapoport et al. |
| 8,812,236 B1 | 8/2014 | Freeman et al. |
| 8,851,018 B2 | 10/2014 | Rapoport et al. |
| 8,896,310 B2 | 11/2014 | Rapoport |
| 9,194,972 B2 | 11/2015 | Van Der Zwaag et al. |
| 9,448,093 B2 | 9/2016 | Rapoport |
| 2002/0173717 A1 | 11/2002 | Rohling et al. |
| 2003/0006768 A1 | 1/2003 | Kleinberg et al. |
| 2004/0090230 A1 | 5/2004 | Appel et al. |
| 2004/0116799 A1 | 6/2004 | Srinivasan |
| 2004/0127786 A1 | 7/2004 | Schmit et al. |
| 2004/0169512 A1 | 9/2004 | Jara |
| 2005/0011283 A1 | 1/2005 | Gysling et al. |
| 2005/0024053 A1 | 2/2005 | Care et al. |
| 2005/0030020 A1 | 2/2005 | Siess et al. |
| 2005/0044957 A1 | 3/2005 | Muldowney |
| 2005/0203420 A1 | 9/2005 | Kleen et al. |
| 2006/0011547 A1 | 1/2006 | Bell |
| 2007/0061081 A1 | 3/2007 | Moran |
| 2007/0164737 A1 | 7/2007 | Pusiol |
| 2008/0136049 A1 | 6/2008 | Yang et al. |
| 2008/0136409 A1 | 6/2008 | Sen et al. |
| 2008/0174309 A1 | 7/2008 | Pusiol et al. |
| 2008/0180226 A1 | 7/2008 | Schmidt |
| 2008/0189456 A1 | 8/2008 | Schmidt et al. |
| 2008/0257413 A1 | 10/2008 | Noureldin et al. |
| 2009/0044638 A1 | 2/2009 | Gysling et al. |
| 2009/0072824 A1 | 3/2009 | Romero |
| 2009/0090504 A1 | 4/2009 | Weightman et al. |
| 2009/0194330 A1 | 8/2009 | Gray |
| 2009/0312963 A1 | 12/2009 | Najim Al-Khamis |
| 2009/0312964 A1 | 12/2009 | Najim Al-Khamis |
| 2010/0133488 A1 | 6/2010 | Giakos |
| 2010/0264914 A1 | 10/2010 | Minh |
| 2011/0036584 A1 | 2/2011 | Weightman et al. |
| 2011/0125333 A1 | 5/2011 | Gray |
| 2011/0162652 A1 | 7/2011 | Rapoport |
| 2011/0185795 A1 | 8/2011 | Colquhoun |
| 2011/0186049 A1 | 8/2011 | Rapoport |
| 2011/0234347 A1 | 9/2011 | Rapoport |
| 2011/0270525 A1 | 11/2011 | Hunter |
| 2011/0296911 A1 | 12/2011 | Moore et al. |
| 2011/0304333 A1 | 12/2011 | Rapoport |
| 2012/0013335 A1* | 1/2012 | Saasen .......... G01N 24/08 324/303 |
| 2012/0024602 A1 | 2/2012 | Larson |
| 2012/0065491 A1 | 3/2012 | Borgert et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0092007 A1 | 4/2012 | Li et al. |
| 2012/0119742 A1 | 5/2012 | Rapoport |
| 2012/0265050 A1 | 10/2012 | Wang |
| 2013/0009959 A1 | 1/2013 | Calamante et al. |
| 2013/0060474 A1 | 3/2013 | Venkataramanan et al. |
| 2013/0079624 A1 | 3/2013 | Rapoport |
| 2013/0090855 A1 | 4/2013 | Rasmus et al. |
| 2013/0091941 A1 | 4/2013 | Huh et al. |
| 2013/0109956 A1 | 5/2013 | Rapoport |
| 2013/0154644 A1 | 6/2013 | Virtanen et al. |
| 2013/0179092 A1 | 7/2013 | Martin et al. |
| 2013/0237803 A1 | 9/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2014/0049257 A1 | 2/2014 | Rapoport |
| 2014/0050824 A1 | 2/2014 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |

(56) References Cited

U.S. PATENT DOCUMENTS

| | | | |
|---|---|---|---|
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport | |
| 2014/0300358 A1 | 10/2014 | Rapoport | |
| 2014/0309951 A1 | 10/2014 | Alvarez-Vallejos et al. | |
| 2014/0333304 A1 | 11/2014 | Jensen | |
| 2014/0354299 A1 | 12/2014 | Rapoport | |
| 2014/0378821 A1 | 12/2014 | Rapoport et al. | |
| 2014/0378825 A1 | 12/2014 | Rapoport et al. | |
| 2015/0059157 A1 | 3/2015 | Rapoport | |
| 2015/0059655 A1 | 3/2015 | Rapoport | |
| 2015/0065788 A1 | 3/2015 | Rapoport | |
| 2015/0084630 A1 | 3/2015 | Rapoport | |
| 2015/0087051 A1 | 3/2015 | Rapoport | |
| 2015/0112186 A1 | 4/2015 | Rapoport et al. | |
| 2015/0137812 A1 | 5/2015 | Rapoport | |
| 2015/0141799 A1 | 5/2015 | Rapoport et al. | |
| 2015/0168519 A1 | 6/2015 | Rapoport | |
| 2015/0268374 A1* | 9/2015 | Rapoport | E21B 49/08 702/6 |
| 2015/0377998 A1* | 12/2015 | Bendel | G01N 24/081 324/324 |
| 2016/0108687 A1* | 4/2016 | Rapoport | E21B 49/00 175/24 |

FOREIGN PATENT DOCUMENTS

| | | |
|---|---|---|
| CN | 1422324 | 6/2003 |
| CN | 1427877 | 7/2003 |
| CN | 1590994 | 3/2005 |
| CN | 101421636 | 4/2009 |
| CN | 101556234 | 10/2009 |
| CN | 101581717 | 11/2009 |
| CN | 101632584 | 1/2010 |
| CN | 101793147 | 8/2010 |
| CN | 101907586 | 12/2010 |
| CN | 103217362 | 7/2013 |
| CN | 103542899 | 1/2014 |
| CN | 103712071 | 4/2014 |
| CN | 103954639 | 7/2014 |
| EP | 0 210 289 | 2/1987 |
| EP | 0770660 | 5/1997 |
| EP | 0835463 | 8/2003 |
| EP | 2604996 | 6/2013 |
| EP | 2927420 A2 | 10/2015 |
| EP | 2927420 A3 | 2/2016 |
| GB | 2341685 A | 7/1999 |
| RU | 2229023 | 5/2004 |
| RU | 2285119 | 10/2006 |
| RU | 2367982 | 9/2009 |
| SU | 876954 | 10/1981 |
| SU | 1041677 | 9/1983 |
| WO | WO1995018387 | 7/1995 |
| WO | WO2001002832 | 1/2001 |
| WO | WO2001051588 | 7/2001 |
| WO | WO2001051589 | 7/2001 |
| WO | WO2008008447 | 1/2008 |
| WO | WO2008043373 | 4/2008 |
| WO | WO2010000055 | 1/2010 |
| WO | WO2011095600 | 8/2011 |
| WO | WO-2013/009299 | 1/2013 |
| WO | WO2013162400 | 10/2013 |
| WO | WO2013179092 | 12/2013 |
| WO | WO2014004573 | 1/2014 |
| WO | WO2014203245 | 12/2014 |
| WO | WO2015070872 | 5/2015 |

OTHER PUBLICATIONS

Pohost et al., "Nuclear Magnetic Resonance Imaging: With or Without Nuclear", IACC vol. 7, No. 3 Mar. 1986, pp. 709-710.*

Coussot et al. "Rheological Behavior of Drilling Muds, Characterization Using MRI Visualization", Oil & Gas Science and Technology—Rev. IFR, vol. 59(1), 2004, pp. 23-29.

Prammer et al. "The Magnetic-Resonance While-Drilling Tool: Theory and Operation", SPE Reservoir Evaluation & Engineering, vol. 4(4), 72495-PA, Aug. 2001.

Shadday Jr., "Recommendations for Rheological Testing and Modelling of DWPF Melter Feed Slurries(U)", Engineering & Materials Technology Department, Aug. 8, 1994, pp. 1-45.

International Search Report for PCT Application No. PCT/IL2004/050544, dated Jan. 7, 2015.

International Search Report dated Jan. 7, 2015 from parent PCT Appl. No. PCT/IL2014/050544.

International Preliminary Report on Patentability dated Jun. 17, 2015 from parent PCT Appl. No. PCT/IL2014/050544.

ANSI/ISA SP76.00.2002 Miniature, Modular Mechanical Standard Specifications, 2002.

Arola et al., Use of nuclear magnetic resonance imaging as a viscometer for process monitoring, Chemical Engineering Science, 1997, 52(13), 2049-2057.

Bennett, et al. A nondestructive technique for determining thermal properties of thermal barrier coatings, Journal of Applied Physics, 2005, 97, 013520,1-12.

Bird et al. Transport Phenomena, Chapter. 2, Shell momentum balances and velocity distributions in laminar flow, Dec. 31, 2002, XP-002768172, Wiley, p. 54.

Caprihan, et al. Flow measurements by NMR, Physics Reports, (Review Section of Physics Letters) 1990, 198(4), 195-235.

Degre et al., Rheology of complex fluids by particle image velocimetry in microchannels, Appl. Phys. Lett. 89(2), 024104, Jan. 3, 2006.

Doble et al., Optimization of the relaxivity of MRI contrast agents: effects of poly(ethylene glycol) chains on the water-exchange rates of Gd complexes, J. Am. Chem. Soc. 2001, 123, 10758-10759.

Dogan et al., Measurement of polymer melt rheology using ultrasonics-based in-line rheometry, Meas. Sci. Technol.,2005, 16(8),1684-1690.

Dyverfeldt et al., Quantification of intravoxel velocity standard deviation and turbulence intensity by generalizing phase-contrast MRI, Magnetic Resonance in Medicine, 2006, 56:850-858.

Felemban, et al. RFID for Oil and Gas Industry: Applications and Challenges, International Journal of Engineering and Innovative Technology (IJEIT) vol. 3, Issue 5, Nov. 2013, 20-85.

Goloshevsky et al., Nuclear magnetic resonance imaging for viscosity measurements of non-Newtonian fluids using a miniaturized RF coil, Meas. Sci. Technol., 2005, 16:513-518.

Gunnerod et al., Highly automated drilling fluids system improves HSE and efficiency, reduced personnel needs, Drilling Contractor, Heath, Safety & Environment, Jan./Feb. 2009, 73-77.

Guzel et al., Predicting laminar-turbulent transition in Poiseuille pipe flow for non-Newtonian fluids, Chemical Engineering Science 2009, 64(2), 254-264.

Hou et al., Review Article, Instrument techniques for rheometry, Review of Scientific Instruments, 2005, 76, 101101, 1-19.

Hsu et al., Encoding to the longitudinal magnetization for MR imaging and flow velocity mapping, Journal of Magnetic Resonance, 2006, 183, 41-49.

International Electromechanical Commission in publication, IEC 62339-1:2006, 2006.

Kose, Katsumi, Visualization of local shearing motion in turbulent fluids using echo-planar imaging, Journal of Magnetic Resonance, 1992, 96, 596-603.

Lucas et al., An Iterative Image Registration Technique with an Application to Stereo Vision, Proceedings of Imaging Understanding Workshop, pp. 121-130 (1981).

MacGowan et al., Fast measurements of the motion and velocity spectrum of blood using MR tagging, Magnetic Resonance in Medicine, 2001, 45:461-469.

Ocali et al., Ultimate intrinsic signal-to-noise ratio in MRI, MRM, 1998, 39:462-473.

Pohost et al., Nuclear magnetic resonance imaging: With or without nuclear?, JACC Mar. 1986, vol. 7, No. 3, 709-710.

(56) References Cited

OTHER PUBLICATIONS

Poole et al., Development-Length Requirements for Fully Developed Laminar Pipe Flow of Inelastic Non-Newtonian Liquids, Journal of Fluids Engineering, Oct. 2007, vol. 129, 1281-1287.
Poulichet et al., Optimisation and realisation of a portable NMR apparatus and Micro Antenna for NMR, DTIP, May 11-13, 2011, Aix-en-Provence, France.
Rabideau et al., The extrusion of a model yield stress fluid imaged by MRI velocimetry, J. Non-Newtonian Fluid Mech, 2010, 165, 394-408.
Yan, Jienian, Drilling Fluids Technology, May 31, 2001, China University of Petroleum Press, pp. 61-66.
Bradley Jr. et al., The appearance of rapidly flowing blood on magnetic resonance images, AJR, Dec. 1984, 143:1167-1174.

\* cited by examiner

NMR/MRI-BASED INTEGRATED SYSTEM FOR ANALYZING AND TREATING OF A DRILLING MUD FOR DRILLING MUD RECYCLING PROCESS AND METHODS THEREOF

FIELD OF THE INVENTION

The present invention generally pertains to (i) an NMR/MRI-based integrated system and to (ii) an NMR/MRI-based and at least one non-NMR/MRI-analysis means integrated system for analyzing and treating of a drilling mud for drilling mud recycling process and to feedbacked methods thereof. The invention also related to means and both physical and chemical methods of analyzing drilled products and for analyzing engineering-related parameters of the drilling.

BACKGROUND OF THE INVENTION

We were learning form Coussot et al., *Oil & Gas Science and Technology—Rev. IFP*, Vol. 59 (2004), No. 1, pp. 23-29, that drilling muds are very complex fluids used to drill oil wells; their functions are various: to carry the rock cuttings to the surface, to maintain a sufficient pressure against the rock formation, to lubricate and cool the bit. There are a few families of drilling muds: oil based muds (invert emulsion of brine into an oil phase with various additives) and water based muds (aqueous solutions of clays and polymers). Originally prepared from produced oil, oil based muds formulations have evolved to very complex compositions of various additives. The base oil may be of various nature, and additives are very complex: water droplets, surfactants, organophilic clays, viscosifyers, various solids and others. These additives give specific properties to the mud, particularly regarding rheological properties. Drilling muds are often described as thixotropic shear thinning fluids with a yield stress. Due to their complex composition, drilling muds exhibit an internal structure which is liable to modify according to the flowing and shear conditions, which may lead to non-homogenous phenomena. It is therefore important to develop investigation techniques allowing visualizing the internal structure of the fluid in parallel to rheological measurements.

Coussot et al further presented rheological experiments coupled to magnetic resonance imaging (MRI). Using this technique, they have determined the velocity profile in a viscometric flow. Coussot et al did not disclose or taught use of MRI in returning mud treatment, as be disclosed below.

More about the aforesaid drilling muds: water-based mud (WBM) is a most basic water-based mud system begins with water, then clays and other chemicals are incorporated into the water to create a homogenous blend resembling something between chocolate milk and a malt (depending on viscosity). The clay (called "shale" in its rock form) is usually a combination of native clays that are suspended in the fluid while drilling, or specific types of clay that are processed and sold as additives for the WBM system. The most common of these is bentonite, frequently referred to in the oilfield as "gel". Gel likely makes reference to the fact that while the fluid is being pumped, it can be very thin and free-flowing (like chocolate milk), though when pumping is stopped, the static fluid builds a "gel" structure that resists flow. When an adequate pumping force is applied to "break the gel", flow resumes and the fluid returns to its previously free-flowing state. Many other chemicals (e.g. potassium formate) are added to a WBM system to achieve various effects, including: viscosity control, shale stability, enhance drilling rate of penetration, cooling and lubricating of equipment. Oil-based mud (OBM) can be a mud where the base fluid is a petroleum product such as diesel fuel. Oil-based muds are used for many reasons, some being increased lubricity, enhanced shale inhibition, and greater cleaning abilities with less viscosity. Oil-based muds also withstand greater heat without breaking down. The use of oil-based muds has special considerations. These include cost, environmental considerations such as disposal of cuttings in an appropriate place to isolate possible environmental contamination and the exploratory disadvantages of using oil based mud, especially in wildcat wells due inability to analyze oil shows in cuttings, because the oil based mud has fluorescence confusing with the original oil of formation. Therefore induces contamination of cuttings samples, cores, sidewall cores for geochemical analysis of TOC and masks the real determination of API gravity due to this contamination. Synthetic-based fluid (SBM) is a mud where the base fluid is a synthetic oil. This is most often used on offshore rigs because it has the properties of an oil-based mud, but the toxicity of the fluid fumes are much less than an oil-based fluid.

On a drilling rig, mud is pumped from the mud pits through the drill string where it sprays out of nozzles on the drill bit, cleaning and cooling the drill bit in the process. The mud then carries the crushed or cut rock ("cuttings") up the annular space ("annulus") between the drill string and the sides of the hole being drilled, up through the surface casing, where it emerges back at the surface. Cuttings are then filtered out with either a shale shaker, or the newer shale conveyor technology, and the mud returns to the mud pits. The mud pits let the drilled "fines" settle; the pits are also where the fluid is treated by adding chemicals and other substances.

The returning mud can contain natural gases or other flammable materials which will collect in and around the shale shaker/conveyor area or in other work areas. Because of the risk of a fire or an explosion if they ignite, special monitoring sensors and explosion-proof certified equipment is commonly installed, and workers are advised to take safety precautions. The mud is then pumped back down the hole and further re-circulated. After testing, the mud is treated periodically in the mud pits to ensure properties which optimize and improve drilling efficiency, borehole stability, and other requirements listed below.

Drilling muds are classified based on their fluid phase, alkalinity, dispersion and the type of chemicals used. Dispersed systems are Freshwater mud—Low pH mud (7.0-9.5) that includes spud, bentonite, natural, phosphate treated muds, organic mud and organic colloid treated mud. High pH mud example alkaline tannate treated muds are above 9.5 in pH. Water based drilling mud that represses hydration and dispersion of clay—There are 4 types: high pH lime muds, low pH gypsum, seawater and saturated salt water muds. Non-dispersed systems are low solids mud—These muds contain less than 3-6% solids by volume and weight less than 9.5 lbs/gal. Most muds of this type are water-based with varying quantities of bentonite and a polymer. Emulsions usually selected from oil in water (oil emulsion muds) and water in oil (invert oil emulsion muds). Oil based muds contain oil as the continuous phase and water as a contaminant, and not an element in the design of the mud. They typically contain less than 5% (by volume) water. Oil-based muds are usually a mixture of diesel fuel and asphalt, however can be based on produced crude oil and mud, see M. G. Prammer, E. Drack, G. et al. 2001. *The Magnetic-*

*Resonance While-Drilling Tool: Theory and Operation, SPE Reservoir Evaluation & Engineering* 4(4) 72495-PA which is incorporated herein as a reference.

U.S. Pat. No. 6,268,726 to Numar Corporation, named "Method and apparatus for nuclear magnetic resonance measuring while drilling" ('726) discloses an NMR measurement-while-drilling tool having the mechanical strength and measurement sensitivity to perform NMR measurements of an earth formation while drilling a borehole, and a method and apparatus for monitoring the motion of the measuring tool in order to take this motion into account when processing NMR signals from the borehole, is incorporated herein as a reference. US '726 further discloses an apparatus wherein its tool has a permanent magnet with a magnetic field direction substantially perpendicular to the axis of the borehole, a steel collar of a non-magnetic material surrounding the magnet, antenna positioned outside the collar, and a soft magnetic material positioned in a predetermined relationship with the collar and the magnet that helps to shape the magnetic field of the tool. Due to the non-magnetic collar, the tool can withstand the extreme conditions in the borehole environment while the borehole is being drilled. Motion management apparatus and method are employed to identify time periods when the NMR measurements can be taken without the accuracy of the measurement being affected by the motion of the tool or its spatial orientation.

Other patents directed to practical NMR measurements while drilling are U.S. Pat. No. 5,705,927 issued Jan. 6, 1998, to Sezginer et al.; U.S. Pat. No. 5,557,201 issued Sep. 17, 1996, to Kleinberg et al.; and U.S. Pat. No. 5,280,243 issued Jan. 18, 1994, to Miller; U.S. Pat. No. 6,362,619 and U.S. Pat. No. 8,373,412, U.S. Pat. No. 8,143,887 "Apparatus and method for real time and real flow-rate measurement of multi-phase fluids with MRI" by Shell Oil Company (Houston, Tex., herein after '887)—all are incorporated herein as a reference.

An MRI/NMR-based means and methods for real-time in-vivo rheology measurements of drilling muds, especially for optimizing the recycling conditions and treatment of the mud, including continuous, one-step on-line measurement of mud-related parameters is still a long felt need. Moreover, such measuring system for defining mud characteristics, such as its fluid phase, alkalinity, dispersion and the type of chemicals used to be further add is an unmet need, currently necessary for optimizing and improve drilling efficiency, borehole stability, and other requirements as stated above.

SUMMARY OF THE INVENTION

It is a first object of the invention to disclose an NMR/MRI-based integrated system for analyzing and treating of a drilling mud for drilling mud recycling line; said system comprising: drilling mud recycling equipment; an NMR/MRI device configured to provide at least one image of at least a portion of said drilling mud at said at least one characterized recycling step in said drilling mud recycling line; and a processor for analyzing and controlling the recycling of said drilling mud; wherein said NMR/MRI-based integrated system is operating in a method of analyzing said NMR/MRI image online; operatively communicating results of said analysis to said drilling mud recycling equipment; and online feedback controlling at least one step in the recycling of said drilling mud recycling equipment, thereby controlling automatically said at least one step in the recycling of said drilling mud recycling.

Another object of the invention is to disclose the system as defined above, wherein said drilling mud recycling steps are selected from a group consisting of adding ingredients and raw materials, mixing, shaking, rotating, tumbling, aerating, heating, cooling, holding at a fixed temperature, emulsifying, adding water or water immiscible solutions, grinding, grounding, milling, shredding, pulvering, cutting, filtering, reducing particle size, de-emulsifying, kneading, decanting, settling, distilling, decentering, vacuuming and any combination thereof.

Another object of the invention is to disclose the system as defined in any of the above, wherein at least one of the following is being held true (a) said NMR/MRI-based means for analyzing at least one criterion, parameter, value or characteristic of the drilling mud generates at least one radial velocity profile from said at least one magnetic resonance image; (b) said means for analyzing criterion, parameter, value or characteristic of the drilling mud generates at least two radial pressure profiles; (c) said NMR/MRI means provides an NMR/MRI image having at least one criterion, parameter, value or characteristic related with said mud's characteristic selected from a group consisting of specific gravity, density, salinity, rheology parameters, particle size, radius and distribution thereof, particles shape, especially particles smoothness versus their roughness, ruggedness, gruffness, choppedness, roughness, granulation, raggedness, raucousness, rustication or scabrousness, water content, content of water-immiscible solutions, water to solvent ratio, and any combination thereof.

Another object of the invention is to disclose the system as defined in any of the above, wherein said means for analyzing at least one criterion, parameter, value or characteristic of the drilling mud generates at least one rheological parameter of said drilling mud from at least one of said at least one radial velocity profile and said at least two radial pressure profiles.

Another object of the invention is to disclose the system as defined in any of the above, wherein said at least one rheological parameter is selected from a group consisting of radial shear stress parameter $\sigma(r)$, radial shear rate parameter $\gamma(r)$, and any combination of thereof.

Another object of the invention is to disclose the system as defined in any of the above, wherein said means for analyzing at least one criterion of said drilling mud generates stress parameters k and n in the power law equation $\sigma(r) = k[\gamma(r)]^n$ from rheological parameters radial shear stress parameter $\sigma(r)$ and radial shear rate parameter $\gamma(r)$.

Another object of the invention is to disclose the system as defined in any of the above, wherein said means for analyzing at least one criterion, parameter, value or characteristic of the drilling mud is further configured to determine at least one quality parameter Q from said at least one rheological parameter.

Another object of the invention is to disclose the system as defined in any of the above, wherein said quality parameter is $Q = \sqrt{k^2 + n^2}$.

Another object of the invention is to disclose the system as defined in any of the above, wherein standard quality parameter $Q_S = \sqrt{k_S^2 + n_S^2}$ is generated from an analysis of a standardized sample of said drilling mud, said analysis of said standardized sample generating standardized stress parameters $k_S$ and $n_S$ in the power law equation $\sigma_S(r) = k_S[\gamma_S(r)]^{n_S}$ from rheological parameters standardized radial shear stress parameter $\sigma_S(r)$ and standardized radial shear rate parameter $\gamma_S(r)$.

Another object of the invention is to disclose the system as defined in any of the above, wherein composition quality parameter $Q_C=\sqrt{k_C^2+n_C^2}$ is generated from analysis of a sample of said drilling mud, said analysis of said sample generating composition stress parameters $k_C$ and $n_C$ in the power law equation $\sigma_C(r)=k_C[\gamma_C(r)]^{n_C}$ from rheological parameters composition radial shear stress parameter $\sigma_C(r)$ and composition radial shear rate parameter $\gamma_C(r)$.

Another object of the invention is to disclose the system as defined in any of the above, wherein a quality test parameter is: $Q_T=|Q_S-Q_C|$.

Another object of the invention is to disclose the system as defined in any of the above, wherein said quality criterion is: said quality test parameter is smaller than one standard deviation of said standard quality parameter.

Another object of the invention is to disclose the system as defined in any of the above, wherein said standard deviation is one standard deviation of either said standard quality parameter or said composition quality parameter.

Another object of the invention is to disclose the system as defined in any of the above, wherein said alterable at least one parameter is selected from a group consisting of addition of an ingredient, the rate of addition of an ingredient, mixing rate, mixing time, raw materials admixing rate, raw materials admixing time, rate of change of mixing rate, shaking rate, shaking time, rate of change of shaking rate, rotation rate, rotation time, rate of change of rotation rate, tumbling rate, tumbling time, rate of change of tumbling rate, aeration rate, aeration time, rate of change of aeration rate, cutting or milling time or rate, heating rate, heating time, rate of change of heating rate, shaking rate, shaking time, rate of change of heating rate, cooling rate, cooling time, rate of change of cooling rate, time held at a constant temperature, emulsification rate de-emulsification rate, emulsification time, de-emulsification time rate of change of emulsification rate, kneading rate, kneading time, rate of change of kneading rate, and any combination thereof.

Another object of the invention is to disclose the system as defined in any of the above, wherein said alterable at least one parameter comprises addition of an ingredient; said ingredient stored in an said ingredient supply system comprising a plurality of ingredient supply reservoirs, each reservoir of said plurality of ingredient supply reservoirs comprising at least one ingredient of said plurality of ingredients.

Another object of the invention is to disclose the system as defined in any of the above, wherein at least one of the following is being held true (a) if said quality parameter satisfies said quality criterion, a further batch of said drilling mud is input to said drilling mud recycling line; (b) if said quality parameter does not satisfy said quality criterion, said processor instructs said ingredient supply system to inject a quantity of at least one ingredient into said composition; (c) said at least one criterion of at least one composition of said food product is selected based on its relationship to at least one of a group consisting of: drilling mud's rheology and drilling-related relevant properties and characteristics thereof; (d) at least a part of said drilling mud recycling equipment is configured to comply with a NeSSI specification; (e) at least a part of said drilling mud recycling equipment is configured to comply with ANSI/ISA SP76.00.2002 miniature, modular mechanical standard specifications; (f) said drilling mud recycling equipment comprises a NeSSI communication bus; and any combination thereof.

Another object of the invention is to disclose the system as defined in any of the above, wherein said NMR/MRI device is connected with said drilling mud recycling line in one or more ways listed in a group consisting of in line connection, on line connection, next to line connection, side-by-side parallel connection, bypass connection and any combination thereof.

Another object of the invention is to disclose the system as defined in any of the above, wherein said NMR/MRI device or devices is connected with said drilling mud recycling line in one or more ways listed in a group consisting of single NMR/MRI device per drilling mud recycling line, a multiple NMR/MRI devices per drilling mud recycling line; either single or multiple manifolds of drilling mud recycling lines, wherein to at least one of said manifolds, either a single or multiple NMR/MRI devices are utilized;

Another object of the invention is to disclose the system as defined in any of the above, wherein at least one NMR/MRI device is in direct connection with the drilling mud recycling line.

Another object of the invention is to disclose the system as defined in any of the above, wherein at least one NMR/MRI device is in indirect connection with the drilling mud recycling line.

Another object of the invention is to disclose the system as defined in any of the above, wherein at least one NMR/MRI device is in indirect connection with the drilling mud recycling line via at least one bypass of said drilling mud recycling line.

Another object of the invention is to disclose the system as defined in any of the above, wherein at least one NMR/MRI device is in online connection with the drilling mud recycling line.

Another object of the invention is to disclose the system as defined in any of the above, wherein at least one NMR/MRI device is in offline connection with the drilling mud recycling line.

Another object of the invention is to disclose the system as defined in any of the above, wherein at least one NMR/MRI device is in connection with more than one drilling mud recycling lines.

Another object of the invention is to disclose the system as defined in any of the above, wherein at least one NMR/MRI device is in connection with two or more different steps of a single drilling mud recycling lines.

Another object of the invention is to disclose the system as defined in any of the above, wherein said NMR/MRI device provides time-resolved images of the mud drilling mud recycling lines.

Another object of the invention is to disclose the system as defined in any of the above, wherein said recycled drilling mud of at least one first drilling is further utilized in said at least one first drilling.

Another object of the invention is to disclose the system as defined in any of the above, wherein said recycled drilling mud of at least one first drilling is further utilized in at least one second drilling, said first and said second drillings are different drillings.

Another object of the invention is to disclose the system as defined in any of the above, wherein said NMR/MRI device provides "an optimal drilling mud" standard.

It is also in the scope of the invention to disclose novel means and both physical- and chemical-methods of analyzing drilled products; and for analyzing engineering-related parameters of the drilling.

Another object of the invention is thus to disclose a system of analyzing drilling parameters, operative in a method which comprising, inter alia, steps as follows: at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole; after flowing period, i.e., time length between drilling mud influx and its outflow out from the hole, at least one step of imaging and timing a series of NMR/MRI images of drilling mud after the use in a drilling hole ($T_{outflow}$); comparing at least one parameter of said inflowing mud (timed at $T_{influx}$ and said outflowing mud timed (timed at $T_{outflow}$); thereby defining the change of said parameter and analyzing parameters related with the drilling (debris shape and size, particle distribution and smoothness etc).

Another object of the invention is to disclose system of analyzing drilled product, operative in a method which comprising, inter alia, steps as follows: at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole, thereby providing said drilling mud as a flowing carrier of the drilled product (such as solid ground, earth samples, water oil, gas, ores, coal etc.), after flowing period, i.e., time length between drilling mud influx and its outflow out from the hole, at least one step of imaging and timing a series of NMR/MRI images of drilling mud after the use in a drilling hole ($T_{outflow}$); and comparing at least one parameter of said inflowing mud (timed at $T_{influx}$) and said outflowing mud timed (timed at $T_{outflow}$); thereby defining the change of said parameter and analyzing said drilled product.

Another object of the invention is to disclose an NMR/MRI-based integrated method for analyzing and treating of a drilling mud in drilling mud recycling process: said method comprises, inter alia, steps as follows: providing a system comprising: drilling mud recycling equipment; an NMR/MRI device configured to provide at least one image of at least a portion of said drilling mud at said at least one characterized recycling step; and a processor for analyzing and controlling the recycling of said drilling mud; analyzing said NMR/MRI image online; operatively communicating results of said analysis to said drilling mud recycling equipment; and online feedback controlling at least one step in the recycling of said drilling mud recycling equipment, thereby controlling automatically said at least one step in the recycling of said drilling mud recycling.

Another object of the invention is to disclose the system as defined in any of the above, wherein the method additionally comprising at least one step selected from a group consisting of (a) selecting said drilling mud recycling steps from a group consisting adding ingredients and raw materials, mixing, shaking, rotating, tumbling, aerating, heating, cooling, holding at a fixed temperature, emulsifying, adding water or water immiscible solutions, grinding, grounding, milling, shredding, pulvering, cutting, filtering, reducing particle size, de-emulsifying, kneading, decanting, settling, distilling, decentering, vacuuming, and any combination thereof; (b) determining a standardized drilling-mud quality parameter, said standardized quality parameter determined from said analysis of said at least one sample of said at least one standardized composition of said drilling-mud; (c) determining a quality criterion from said analysis of said at least one sample of said at least one standardized composition of said drilling-mud; (e) analyzing said composition of said drilling-mud to generate at least one radial velocity profile of said composition of said drilling-mud from said at least one magnetic resonance image; and any combination thereof; and (d) providing an NMR/MRI image having at least one criterion, parameter, value or characteristic related with said mud's characteristic selected from a group consisting of specific gravity, density, salinity, rheology parameters, particle size, radius and distribution thereof, particles shape, especially particles smoothness versus their roughness, ruggedness, gruffness, roughness, granulation, raggedness, raucousness, rustication or scabrousness, water content, content of water-immiscible solutions, water to solvent ratio, and any combination thereof.

Another object of the invention is to disclose the system as defined in any of the above, wherein the method additionally comprising a step of generating at least two radial pressure profiles of said composition of said drilling-mud.

Another object of the invention is to disclose the system as defined in any of the above, wherein the method additionally comprising a step generating at least one rheological parameter of said composition of said drilling-mud from at least one of said at least one radial velocity profile and said at least two radial pressure profiles.

Another object of the invention is to disclose the system as defined in any of the above, wherein the method additionally comprising at least one step selected from a group consisting of (a) selecting said at least one rheological parameter from a group consisting of radial shear stress parameter $\sigma(r)$, radial shear rate parameter $\gamma(r)$, and any combination of thereof; (b) generating stress parameters k and n in the power law equation $\sigma(r)=k[\gamma(r)]^n$ from rheological parameters radial shear stress parameter $\sigma(r)$ and radial shear rate parameter $\gamma(r)$; and any combination thereof.

Another object of the invention is to disclose the system as defined in any of the above, wherein the method additionally comprising a step of determining at least one quality parameter Q from said at least one rheological parameter.

Another object of the invention is to disclose the system as defined in any of the above, wherein the method additionally comprising a step of generating said quality parameter from $Q=\sqrt{k^2+n^2}$.

Another object of the invention is to disclose the system as defined in any of the above, wherein the method additionally comprising a step of generating standard quality parameter $Q_S=\sqrt{k_S^2+n_S^2}$ from analysis of a standardized sample of said drilling-mud, said analysis of said standardized sample generating standardized stress parameters $k_S$ and $n_S$ in the power law equation $\sigma_S(r)=k_S[\gamma_S(r)]^{n_s}$ from rheological parameters standardized radial shear stress parameter $\sigma_S(r)$ and standardized radial shear rate parameter $\gamma_S(r)$.

Another object of the invention is to disclose the system as defined in any of the above, wherein the method additionally comprising a step of generating drilling-mud quality parameter $Q_C=\sqrt{k_C^2+n_C^2}$ from analysis of a sample of said drilling-mud, said analysis of said drilling-mud sample generating drilling-mud stress parameters $k_C$ and $n_C$ in the power law equation $\sigma_C(r)=k_C[\gamma_C(r)]^{n_C}$ from rheological parameters drilling-mud radial shear stress parameter $\sigma_C(r)$ and drilling-mud radial shear rate parameter $\gamma_C(r)$.

Another object of the invention is to disclose the system as defined in any of the above, wherein the method additionally comprising a step of generating quality test parameter $Q_T=|Q_S-Q_C|$.

Another object of the invention is to disclose the system as defined in any of the above, wherein the method additionally comprising at least one step selected from a group consisting of (a) setting said quality criterion as: said quality test parameter is smaller than one standard deviation of said standard quality parameter; (b) setting said quality criterion as: said quality test parameter is smaller than one standard deviation of said drilling-mud quality parameter; and any combination thereof.

Another object of the invention is to disclose the system as defined in any of the above, wherein the method additionally comprising a step of selecting said alterable at least one parameter from a group consisting of (a) selecting said drilling mud recycling steps from a group consisting adding ingredients and raw materials, mixing, shaking, rotating, tumbling, aerating, heating, cooling, holding at a fixed temperature, emulsifying, adding water or water immiscible solutions, grinding, grounding, milling, shredding, pulvering, cutting, filtering, reducing particle size, de-emulsifying, kneading, decanting, settling, distilling, decentering, vacuuming, and any combination thereof; (b) determining a standardized drilling-mud quality parameter, said standardized quality parameter determined from said analysis of said at least one sample of said at least one standardized composition of said drilling-mud; (c) determining a quality criterion from said analysis of said at least one sample of said at least one standardized composition of said drilling-mud; (e) analyzing said composition of said drilling-mud to generate at least one radial velocity profile of said composition of said drilling-mud from said at least one magnetic resonance image; and any combination thereof.

Another object of the invention is to disclose the system as defined in any of the above, wherein the method additionally comprising a step of selecting addition of an ingredient as at least one said alterable at least one parameter; said ingredient stored in an said ingredient supply system comprising a plurality of ingredient supply reservoirs, each reservoir of said plurality of ingredient supply reservoirs comprising at least one ingredient of said plurality of ingredients.

Another object of the invention is to disclose the system as defined in any of the above, wherein the method additionally comprising at least one step selected from a group consisting (a) inputting a further batch of said drilling mud to said drilling mud recycling line if said quality parameter satisfies said quality criterion; (b) injecting a quantity of at least one ingredient into said drilling mud if said quality parameter does not satisfy said quality criterion; (c) selecting said at least one criterion of said drilling mud on its relationship to at least one of a group consisting of: drilling mud's rheology and drilling-related relevant properties and characteristics thereof; (d) configuring at least a part of said food production equipment to comply with a NeSSI specification; (e) configuring at least a part of said food production equipment to comply with ANSI/ISA SP76.00.2002 miniature, modular mechanical standard specifications; (0 providing at least a part of said food production equipment with a NeSSI communication bus; (g) repeating said comparing and said adjusting iteratively for each remaining batch of said plurality of batches; (h) selecting at least one drilling mud criterion in accordance with customer requirements; (i) selecting at least one drilling mud criterion from a group consisting of: drilling mud's rheology and drilling-related relevant properties and characteristics thereof.

Another object of the invention is to disclose the system as defined in any of the above, wherein the method additionally comprising at least one step of connecting said NMR/MRI device with said drilling mud recycling line in one or more ways listed in a group consisting of in line connection, on line connection, next to line connection, side-by-side parallel connection, bypass connection and any combination thereof.

Another object of the invention is to disclose the system as defined in any of the above, wherein the method additionally comprising at least one step of connecting said NMR/MRI device or devices with said drilling mud recycling line in one or more ways listed in a group consisting of single NMR/MRI device per drilling mud recycling line, a multiple NMR/MRI devices per drilling mud recycling line; either single or multiple manifolds of drilling mud recycling lines, wherein to at least one of said manifolds, either a single or multiple NMR/MRI devices are utilized;

Another object of the invention is to disclose the system as defined in any of the above, wherein the method additionally comprising at least one step of connecting said NMR/MRI device in direct connection with the drilling mud recycling line.

Another object of the invention is to disclose the system as defined in any of the above, wherein the method additionally comprising at least one step of connecting said NMR/MRI device indirect connection with the drilling mud recycling line.

Another object of the invention is to disclose the system as defined in any of the above, wherein at least one NMR/MRI device is in indirect connection with the drilling mud recycling line via at least one bypass of said drilling mud recycling line.

Another object of the invention is to disclose the system as defined in any of the above, wherein the method additionally comprising at least one step of connecting said NMR/MRI device in online connection with the drilling mud recycling line.

Another object of the invention is to disclose the system as defined in any of the above, wherein the method additionally comprising at least one step of connecting said NMR/MRI device offline connection with the drilling mud recycling line.

Another object of the invention is to disclose the system as defined in any of the above, wherein the method additionally comprising at least one step of connecting said NMR/MRI device with more than one drilling mud recycling lines.

Another object of the invention is to disclose the system as defined in any of the above, wherein the method additionally comprising at least one step of connecting said NMR/MRI device with two or more different steps of a single drilling mud recycling lines.

Another object of the invention is to disclose the system as defined in any of the above, wherein the method additionally comprising at least one step of providing one or more time-resolved images of the mud drilling mud recycling lines.

Another object of the invention is to disclose the system as defined in any of the above, wherein the method additionally comprising at least one step of imaging and timing a series of NMR/MRI images of drilling mud before mud's re-used in a drilling hole ($T_{influx}$), and at least) one step of imaging and timing a series of NMR/MRI images of drilling mud after the use in a drilling hole ($T_{outflow}$).

Another object of the invention is to disclose the system as defined in any of the above, wherein the method additionally comprising at least one step of utilizing said NMR/MRI device of at least one first drilling in said at least one first drilling.

Another object of the invention is to disclose the system as defined in any of the above, wherein the method additionally comprising at least one step of utilizing said NMR/MRI device of at least one first drilling in said at least one second drilling; said first and said second drillings are different drillings.

Another object of the invention is to disclose the system as defined in any of the above, wherein the method additionally comprising standardizing "an optimal drilling mud".

Another object of the invention is to disclose a method of analyzing drilling parameters, comprising, inter alia, steps as follows: at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole; after flowing period, i.e., time length between drilling mud influx and its outflow out from the hole, at least one step of imaging and timing a series of NMR/MRI images of drilling mud after the use in a drilling hole ($T_{outflow}$); comparing at least one parameter of said inflowing mud (timed at $T_{influx}$) and said outflowing mud timed (timed at $T_{outflow}$); thereby defining the change of said parameter and analyzing parameters related with the drilling (debris shape and size, particle distribution and smoothness etc).

Another object of the invention is to disclose method of analyzing drilled product, comprising at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole, thereby providing said drilling mus as a flowing carrier of the drilled product (such as solid ground, earth samples, water oil, gas, ores, coal etc), after flowing period, i.e., time length between drilling mud influx and its outflow out from the hole, at least one step of imaging and timing a series of NMR/MRI images of drilling mud after the use in a drilling hole ($T_{outflow}$); and comparing at least one parameter of said inflowing mud (timed at $T_{influx}$) and said outflowing mud timed (timed at $T_{outflow}$); thereby defining the change of said parameter and analyzing said drilled product.

Another object of the invention is to disclose method as defined in any of the above, wherein said step of comparing at least one parameter of said inflowing mud (timed at $T_{influx}$) and said outflowing mud timed (timed at $T_{outflow}$) further comprising step of measuring the relaxation time T1, T2 and diffusion coefficient D.

Another object of the invention is to disclose the system as defined in any of the above, wherein the system is integrating (a) NMR, MRI and (b) non-magnetic analytical means.

Another object of the invention is to disclose the system as defined in any of the above, wherein the system comprises analytical means to detect in real-time, non-invasively and/or non intrusionly (i.e., with no obstruction) one or more parameters selected from a group consisting of flow rate, density, water cut (water ratio), rheology, viscosity, particle sizing, salinity and any combination thereof.

Another object of the invention is to disclose an NMR/MRI-based integrated method for analyzing and treating of a drilling mud in drilling mud recycling process: providing a system comprising: drilling mud recycling equipment; an NMR/MRI device configured to provide at least one image of at least a portion of said drilling mud at said at least one characterized recycling step; non-magnetic (non-MRI/NMR) analysis means; and a processor for analyzing and controlling the recycling of said drilling mud; analyzing said NMR/MRI image online; by means of said non-magnetic analysis means, analyzing one or more parameters selected from a group consisting of flow rate, density, water cut (water ratio), rheology, viscosity, particle sizing, salinity and any combination thereof; operatively communicating results of said analysis to said drilling mud recycling equipment; and online feedback controlling at least one step in the recycling of said drilling mud recycling equipment, thereby controlling automatically said at least one step in the recycling of said drilling mud recycling.

Another object of the invention is to disclose a method of analyzing drilling parameters, comprising at least one step of imaging and timing a series of both (i) NMR/MRI images and (ii) non-magnetic (non-MRI/NMR) analysis means, of drilling mud before mud's re-used in a drilling hole ($T_{influx}$); either continuously of batch-wise flowing said time-resolved imaged drilling mud within said drilling hole whilst drilling said hole; after flowing period, i.e., time length between drilling mud influx and its outflow out from the hole, at least one step of imaging and timing a series of NMR/MRI images of drilling mud after the use in a drilling hole ($T_{outflow}$); comparing at least one parameter of said inflowing mud (timed at $T_{influx}$) and said outflowing mud timed (timed at $T_{outflow}$); thereby defining the change of said parameter and analyzing parameters related with the drilling.

Another object of the invention is to disclose a method of analyzing drilled product, comprising at least one step of imaging and timing a series of both (i) NMR/MRI images and (ii) non-magnetic (non-MRI/NMR) analysis means, of drilling mud before mud's re-used in a drilling hole ($T_{influx}$); either continuously of batch-wise flowing said time-resolved imaged drilling mud within said drilling hole whilst drilling said hole, thereby providing said drilling mus as a flowing carrier of the drilled product; after flowing period, i.e., time length between drilling mud influx and its outflow out from the hole, at least one step of imaging and timing a series of NMR/MRI images of drilling mud after the use in a drilling hole ($T_{outflow}$); and comparing at least one parameter of said inflowing mud (timed at $T_{influx}$) and said outflowing mud timed (timed at $T_{outflow}$); thereby defining the change of said parameter and analyzing said drilled product.

Another object of the invention is to disclose the an NMR/MRI-based integrated method for analyzing and treating of a drilling mud in drilling mud recycling process as defined in any of the above; wherein the method further comprising step of providing said system with one or more non-magnetic (non-MRI/NMR) analysis means.

Another object of the invention is to disclose the an NMR/MRI-based integrated method for analyzing and treating of a drilling mud in drilling mud recycling process as defined in any of the above; wherein the method further steps of providing said system with one or more non-magnetic (non-MRI/NMR) analysis means; and by means of said non-magnetic analysis means, analyzing one or more parameters selected from a group consisting of flow rate, density, water cut (water ratio), rheology, viscosity, particle sizing, salinity and any combination thereof.

Another object of the invention is to disclose the an NMR/MRI-based integrated method for analyzing and treating of a drilling mud in drilling mud recycling process: providing a system comprising: drilling mud recycling equipment; an NMR/MRI device configured to provide at least one image of at least a portion of said drilling mud at said at least one characterized recycling step; non-magnetic (non-MRI/NMR) analysis means; and a processor for analyzing and controlling the recycling of said drilling mud; analyzing said NMR/MRI image online; by means of said non-magnetic analysis means, analyzing one or more parameters selected from a group consisting of flow rate, density, water cut (water ratio), rheology, viscosity, particle sizing, salinity and any combination thereof; operatively communicating results of said analysis to said drilling mud recycling equipment; and online feedback controlling at least one step in the recycling of said drilling mud recycling equipment, thereby controlling automatically said at least one step in the recycling of said drilling mud recycling.

Another object of the invention is to disclose the a method of analyzing drilling parameters, comprising at least one step of imaging and timing a series of both (i) NMR/MRI images and (ii) non-magnetic (non-MRI/NMR) analysis means, of drilling mud before mud's re-used in a drilling hole ($T_{influx}$); either continuously of batch-wise flowing said time-resolved imaged drilling mud within said drilling hole whilst drilling said hole; after flowing period, i.e., time length between drilling mud influx and its outflow out from the hole, at least one step of imaging and timing a series of NMR/MRI images of drilling mud after the use in a drilling hole ($T_{outflow}$); comparing at least one parameter of said inflowing mud (timed at $T_{influx}$) and said outflowing mud timed (timed at $T_{outflow}$); thereby defining the change of said parameter and analyzing parameters related with the drilling.

Another object of the invention is to disclose the a method of analyzing drilled product, comprising at least one step of imaging and timing a series of both (i) NMR/MRI images and (ii) non-magnetic (non-MRI/NMR) analysis means, of drilling mud before mud's re-used in a drilling hole ($T_{influx}$); either continuously of batch-wise flowing said time-resolved imaged drilling mud within said drilling hole whilst drilling said hole, thereby providing said drilling mus as a flowing carrier of the drilled product; after flowing period, i.e., time length between drilling mud influx and its outflow out from the hole, at least one step of imaging and timing a series of NMR/MRI images of drilling mud after the use in a drilling hole ($T_{outflow}$); and comparing at least one parameter of said inflowing mud (timed at $T_{influx}$) and said outflowing mud timed (timed at $T_{outflow}$); thereby defining the change of said parameter and analyzing said drilled product.

BRIEF DESCRIPTION OF THE DRAWINGS

A preferred embodiment of the current invention is described hereinbelow with reference to the following drawings.

DETAILED DESCRIPTION OF THE PREFERRED EMBODIMENTS

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a means and method for integrating analysis and production of a food product.

In some embodiments, an ingredient processing system interfaces between a mixing vat system of the food production line and the magnetic resonance device, which generates magnetic resonance images of the food flow, from which rheological parameters of the food product are determined. The ingredient processing system fulfills the NeSSI protocols and requirements.

In the present invention, recent developments in industrial process improvement initiatives are adopted such as incorporating an on-line testing and adjusting system for iteratively adjusting the food product's ingredients. Another recent development incorporated in the present invention is the integration of sensing devices and monitoring processes into the sampling system. The mechanism preferably adopted is the NeSSI (New Sensors/Sampling Initiative).

The NeSSI (New Sampling/Sensor Initiative) requirements fulfill the ANSI/ISA SP76.00.2002 miniature, modular mechanical standard and include mechanical systems associated with the fluid handling components. The ANSI/ISA standard is referenced by the International Electrotechnical Commission in publication IEC 62339-1:2006. Preferably, the food production line uses mechanical designs based on the ANSI/ISA SP76.00.02-2002 Standard.

The NeSSI platform is a miniaturized, modular version of traditional sample gathering and handling methodologies, thus permitting the addition of components as standard modules, and the integration of the sensing system with the sampling system to form a single stand-alone unit for sample extraction and measurement. Using the NeSSI platform, process corrections may be detected earlier in the food product production line, thereby minimizing defective food production and food wastage.

The Magnetic Resonance Device (MRD) of Aspect Imaging Ltd (IL and US) is typically useful for the drilling mud analysis, especially, as in the present invention, for managing ingredients. The MRD is a relatively small nuclear magnetic resonance device with about 1 Tesla magnetic field, on the order of 0.5 m×0.5 m×1 m in size. Thus, the MRD device is ideal for incorporating in an on-line system, especially, in the drilling mud recycling line.

The radial shear stress distribution σ(r) is determined from $$\sigma(r) = -\frac{\Delta P(r)}{2L} r, \qquad (1)$$

where ΔP(r) is the pressure difference between entrance port 64 and exit port 66 of the MRD 26 at radial location r. Pressure sensors are located in proximity to the ports 64 and 66 and the pressure sensors measure an axial pressure profile P(r), as is known in the art. The pressure sensors are separated by a distance L.

The radial shear rate γ(r) distribution is determined from $$\dot{\gamma}(r) = \frac{dv(r)}{dr}. \qquad (2)$$

where υ(r) is the radial velocity profile 40.

The NMR images 38, the radial velocity profiles υ(r) 40, the pressure profiles P(r), the distance L, and the rheological parameters σ(r) and γ(r) can be stored in the memory 44 and can be retrieved from memory as required.

According to a power law distribution for the radial shear stress σ(r), the radial shear stress σ(r) and the radial shear rate γ(r) are related:

$$\sigma(r) = k[\gamma(r)]^n, \quad (3)$$

where k and n are the power law stress parameters.

Typically, the parameters k and n are determined by fitting an averaged radial shear rate distribution γ(r) and an averaged shear stress distribution σ(r) for the radial values r to the power law distribution in equation (3).

A useful quality parameter, Q, is $$Q = \sqrt{k^2 + n^2} \quad (4)$$

where k and n are found by fitting the averaged radial shear rate distribution γ(r) and the averaged shear stress distribution σ(r) for the radial values r to the power law distribution in equation (3).

In this embodiment, a composition quality parameter, $Q_C$, is compared to a standard quality parameter, $Q_S$, where $Q_C$ is $$Q_C = \sqrt{k_C^2 + n_C^2} \quad (5)$$

and $Q_S$ is $$Q_S = \sqrt{k_S^2 + n_S^2}. \quad (6)$$

In order to determine whether the sample fulfills the criteria, a quality test parameter $Q_T$ is compared to a check criterion δ and the sample is acceptable if $$Q_T < \delta \quad (7)$$

In one embodiment, $$Q_T = |Q_S - Q_C| \quad (8)$$

and the check criterion is one standard deviation of the standard quality parameter $Q_S$.

In embodiments where the check criterion δ is one standard deviation of the standard quality parameter $Q_S$, the standard quality parameter $Q_S$ is measured for a plurality of standardized samples of the composition and a standard quality parameter $Q_{S,i}$ is determined for each sample i. The standard deviation, $D_s$, of the standard quality parameter $Q_S$ is found, as is known in the art, from the equation $$D_s = \sqrt{\frac{1}{N-1} \sum_{i=1}^{N} (Q_{S,i} - Q_S)^2} \quad (9)$$

where $Q_{S,i}$ is the standard quality parameter for the ith standardized sample of the food product, N is the number of standardized samples tested, and $Q_S$ is the mean of the standard quality parameters $Q_{S,i}$.

In another embodiments, the check criterion is two standard deviations (95%) of the standard quality parameter $Q_S$. In yet other embodiments, 3 or 4 standard deviations, or even more, are used as a check criterion.

Figure 1:
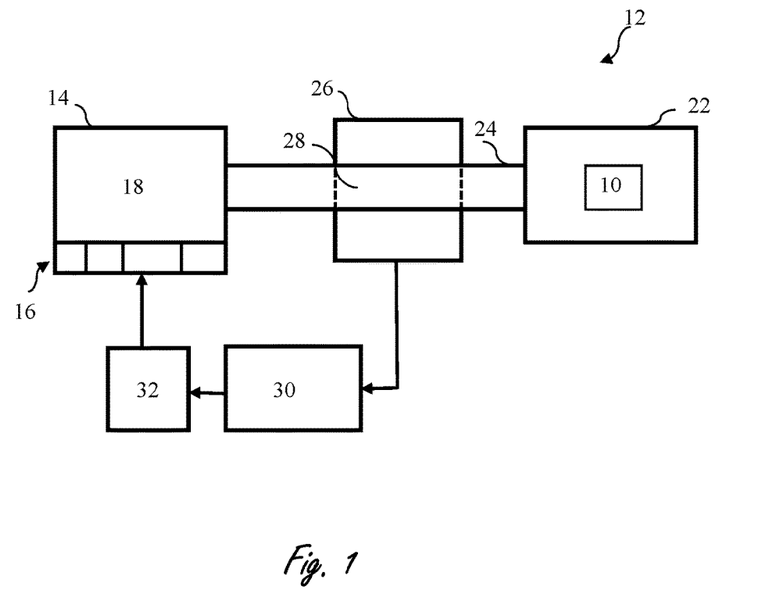
FIG. 1 shows a system for drilling mud recycling line, in accordance with a preferred embodiment of the present invention.

Reference is now made to FIG. 1, which shows an embodiment of the system. In this embodiment, the drilling mud 10 is in a drilling mud recycling line 12. The drilling mud recycling line 12 comprises an ingredient supply device 32, a drilling mud mixing vat system 14, a flow conduit 24, and a drilling mud recycling equipment 22. It also comprises a magnetic resonance imaging device 26 encompassing at least a portion 28 of the flow conduit 24 and a processing system 30. During operation of the drilling mud recycling line, a plurality of raw materials ingredients 16 are injected into the mixing vat system 14, and are mixed until they form a drilling mud 18 of recycled drilling mud 10. The drilling mud 18 is then injected via conduit 24 into drilling mud recycling equipment 22 and drilling mud 10 is produced in drilling mud recycling equipment 22.

The magnetic image resonance device 26 monitors the process in situ, on line and in real time. A sample of drilling mud 18 is injected into flow conduit 24, such that the magnetic resonance imaging device 26 generates at least on magnetic resonance image of the drilling mud 18 flowing through the conduit 24. The processing system 30 processes the at least one magnetic resonance image of the sample of the drilling mud 18 to generate a quality test parameter $Q_T$, of the composition 18, as described below. The quality test parameter $Q_T$ is compared to a predetermined check value $Q_C$, as described below, and if the difference is greater than a predetermined amount, the ingredient supply device 32 is instructed to supply a predetermined amount of at least one ingredient 16 to mixing vat system 14. When the ingredient 16 has been incorporated into drilling mud 18, another sample of drilling mud 18 is injected into flow conduit 24, another at least one magnetic resonance image is generated, and the process is repeated iteratively until the quality test parameter $Q_T$ differs from the predetermined check value $Q_C$ by less than the predetermined amount. In a batch system, the process will terminate when mixing vat system 14 is empty, although no adjustments to the composition 18 are expected to be necessary after an acceptable composition has been attained, and the process will recommence when mixing vat system 14 has been refilled and a new batch of composition 18 has been produced. In a continuous process, there is continuous injection of ingredients 16 into mixing vat system 14, so that the contents of mixing vat system 14 are constantly being replenished.

The drilling mud recycling system 30 is configured to comply with ANSI/ISA SP76.00.2002 miniature, modular mechanical standard specifications.

Figure 2:
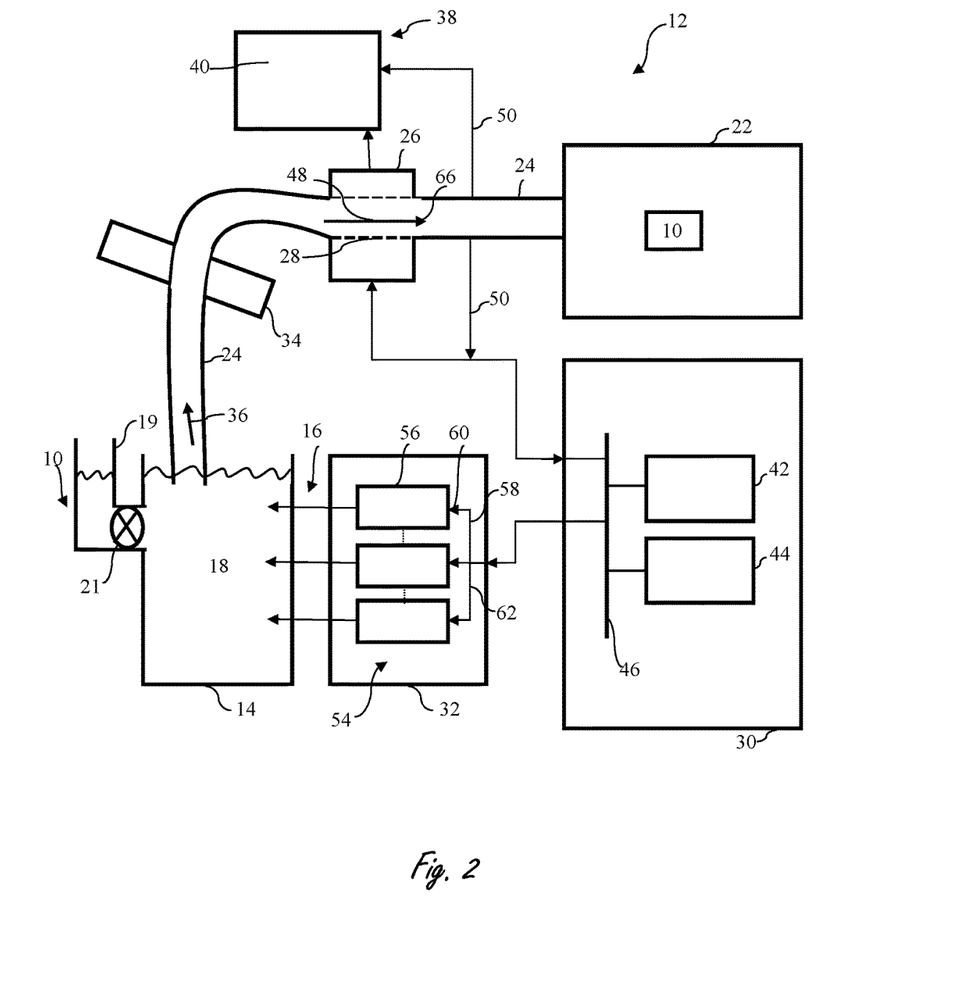
FIG. 2 presents further details of drilling mud recycling line, in accordance with a preferred embodiment of the present invention.

Reference is now made to FIG. 2, which presents further details of the drilling mud recycling line 12, in accordance with a preferred embodiment of the present invention. As shown in FIG. 2, the drilling mud recycling line 12 comprises a vat 14, a batch manifold 19 and control valve 21, a pump 34, a conduit 24, and a food production device 22. It further comprises an ingredient processing system 30 and an ingredient supply device 32.

The ingredient processing system 30 comprises a processor 42, a memory unit 44 and a communications bus 46, such as a NeSSI communications bus, enabling communications between all parts of the system.

The ingredient processing system 30 communicates with the ingredient supply device 32 by means of a communications line 52. The ingredient supply device 32 comprises a plurality of N ingredient reservoirs 54. Typically, each reservoir 56 contains at least one ingredient, $I_{i=j}$. Each reservoir 56 includes a communications port 60, through which each reservoir 56 communicates with the communications line 52 via an internal communication bus 62.

In some embodiments, at least one reservoir 56 contains a mixture of at least two ingredients, $I_{i=j, \, i=m}$.

A batch of a sample of the drilling mud 10 is input into the vat 14 from a batch manifold 19 via a control valve 21. A pump 34 pumps the drilling mud 18 of the sample from the vat 14 to the food production line 22 via nuclear magnetic imaging device 26. A drilling mud flow 36 flows through the conduit 24. At least a portion, 48, of flow 36 passes through at least a portion of nuclear magnetic imaging device 26, between entrance port 64 and exit port 66.

In further reference to FIG. 2, the nuclear magnetic imaging device 26, which can be an NMR device, generates at least one magnetic resonance image 38 of the portion 48 of drilling mud flow 36 within the NMR device as a function of a radial location r, as is known in the art. The at least one magnetic resonance image 38 is processed by processor 42 to determine at least one radial velocity profile, υ(r), 40 of the composition 18, where the radial parameter r is measured from the center of the conduit 24, such that r=0 is the center of the conduit 24 and r=R is the edge of the flow 36. The at least one magnetic resonance image 38 is transferred to the processor 42 via communication line 50 and communication bus 46. In some embodiments, communication line 50 comprises part of communication bus 46.

As said above, drilling mud is used to control subsurface pressures, lubricate the drill bit, stabilize the well bore, and carry the cuttings to the surface, among other functions. As the drill bit grinds rocks into drill cuttings, these cuttings become entrained in the mud flow and are carried to the surface. In order to return the mud to the recirculating mud system and to make the solids easier to handle, the solids must be separated from the mud.

It is thus according to one embodiment of the invention, wherein the following system is provided useful: In order to recycle drilling mud, solids control equipment are used, and a typical four stage solids control equipment used. In a first stage: Shale shaker is utilized: according to rig size, 1 to 3 sets shale shaker will be used at the first stage solids control separation, e.g., this is done with an API 4-0 60 shaker screens. Cutting over 400 μm are separated in this stage. Then a desander and desilter are used as the second and third stage separation. A mud cleaner are utilized for these stages. It is a combination of shake shaker, desander and desilter. For smaller size rigs (usually, under 750 hp), mud treated by shale shaker and mud cleaner can be used for drilling. In some condition, while drilling depth is big, and high standard mud request, decantering centrifuge will be used as forth stage separation. Finer solids are to be separated. For gas cut drilling mud, vacuum degasser, poor degasser and ignition device will be used.

In parallel to the said mud-recycling scheme, an NMR/MRI-analyzing system is integrally utilized to improve the recycle of the used drilling mud and to restore its characteristics to a predefined scale of characteristics, by following the following scheme: (i) defining parameters and values of optimal frilling mud; (ii) on-line and in situ analyzing parameters and values of used frilling mud, preferably, yet not exclusively, along the initial stages of the recycle, when the drilling mud exit from the drilling hole; (iii) comparing said optimal parameters and values and said on-line acquired parameters and values, namely determining the differences between those predefined parameters and value of the 'optimal drilling mud' and correspondent parameters and value of the 'actual drilling mud', thereby defining which recycle step is required, and further defying parameters and values; such as recycling temperature, operation time of each of the recycling steps, type and quantity of raw materials to admix with said mud, admixing parameters etc, wherein the raw materials can be selected from water, bentonite and the like, calcium containing salts and compositions thereof, surfactant (anionic, cationic or zwitterionic surfactants, for example), fresh drilling mud, water immiscible solutions etc. (iv) recycling the used drilling mud whilst continuously NMR/MRI analyzing its properties, thus on-line feedbacking the recycling system, until the characteristics of the recycled drilling mud equal (plus minus an allowable predefined measure) the stored characteristics of the 'optimal drilling mud'. Thus, this novel NMR/MRI-drilling mud recycling integrated-system, provides an on-line, in-situ, one-continuous-step drilling when an optimal drilling mud is utilized, namely a drilling mud having predefined characteristics, such as rheological characteristics, fluid phase characteristics, alkalinity (calcium content and the such), dispersion characteristics and so on and so forth.

EP patent 0835463 discloses that NMR logging is a known method to determine these and other geologic formation parameters of interest. It is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter T1, known as the spin-lattice relaxation time. Another related and frequently used NMR logging parameter is the so called spin-spin relaxation time constant T2 (also known as transverse relaxation time) which is related to the relaxation due to non-homogeneities in the local magnetic field over the sensing volume of the logging tool. The '463 patents further discloses a formation diffusion D which is dependent on the pore sizes of the formation. Mechanisms which determine the values of T1, T2 and D depend on the molecular dynamics of the sample being tested. In bulk volume liquids, typically found in large pores of the formation, molecular dynamics is a function of molecular size and inter-molecular interactions which are different for each fluid. Thus, water and different types of oil each have different T1, T2 and D values.

According to one embodiment of the invention, thus, a time resolved or no-time resolved methods of analyzing drilling parameters, is provided useful, especially as defined in the integrated NMR/MRI drilling mud recycling system the above. The method comprising, inter alia, the following steps: at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole; after flowing period, i.e., time length between drilling mud influx and its outflow out from the hole, at least one step of imaging and timing a series of NMR/MRI images of drilling mud after the use in a drilling hole ($T_{outflow}$); comparing at least one parameter of said inflowing mud (timed at $T_{influx}$) and said outflowing mud timed (timed at $T_{outflow}$); thereby defining the change of said parameter and analyzing parameters related with the drilling: such as debris shape and size, particle distribution and smoothness etc.

According to another embodiment of the invention, a similar method of analyzing drilled product is presented. This method comprises, inter alia, the following steps: at least one step of imaging and timing a series of NMR/MRI images of drilling mud before mud's re-used in a drilling hole ($T_{influx}$); either continuously of batch-wise flowing said time-resolved imaged drilling mud within said drilling hole whilst drilling said hole, thereby providing said drilling mus as a flowing carrier of the drilled product: such as solid ground, earth samples, water oil, gas, ores, coal etc); after flowing period, i.e., time length between drilling mud influx and its outflow out from the hole, at least one images of drilling mud after the use in a drilling hole ($T_{outflow}$); and then comparing at least one parameter of said inflowing mud (timed at $T_{influx}$) and said outflowing mud timed (timed at $T_{outflow}$); thereby defining the change of said parameter and analyzing said drilled product.

In those methods, the aforesaid step of comparing at least one parameter of said inflowing mud (timed at $T_{influx}$) and said outflowing mud timed (timed at $T_{outflow}$) may further comprising a step of measuring the relaxation time T1, T2 and diffusion coefficient D as discussed above. step of imaging and timing a series of NMR/MRI

The invention claimed is:

1. A system for analyzing and treating drilling mud in a drilling mud recycling
line, said system comprising:
a drilling mud recycling line comprising drilling mud recycling equipment configured to perform a process of recycling said drilling mud;
an MRI device configured to provide at least one image of at least a portion of said drilling mud in said drilling mud recycling line; and
a processor for analyzing and controlling recycling of said drilling mud,
wherein said system is configured to perform an analysis of said at least one image online to communicate results of said analysis to said drilling mud recycling equipment, said results comprising at least one value of at least one rheological parameter of said drilling mud, generate at least two radial pressure profiles of said drilling mud, and to control via online feedback at least one step of said process of recycling said drilling mud according to said results.

2. The system according to claim 1, wherein said at least one step of said
process of recycling drilling mud is selected from the group consisting of adding ingredients to said drilling mud, mixing, shaking, rotating, tumbling, aerating, heating, cooling, holding at a fixed temperature, emulsifying, adding water or water immiscible solutions, grinding, grounding, milling, shredding, pulverizing, cutting, filtering, reducing particle size, de-emulsifying, kneading, decanting, settling, distilling, decentering, vacuuming and any combination thereof.

3. The system according to claim 1, wherein said at least one value of said
at least one rheological parameter is calculated from at least one radial velocity profile derived from said at least one image and at least two radial pressure profiles.

4. The system according to claim 1, wherein said at least one rheological
parameter is selected from the group consisting of:
radial shear stress parameter $\sigma(r)$;
radial shear rate parameter $\gamma(r)$;
stress parameters k and n calculated from a power law equation $\delta(r)=k[\gamma(r)]^n$;
at least one quality parameter Q, where $Q=\sqrt{k^2+n^2}$.

5. The system according to claim 1, wherein at least one of the following is true:
at least part of said drilling mud recycling equipment is configured to comply with a NeSSI specification; and,
at least a part of said drilling mud recycling equipment is configured to comply with ANSI/ISA SP76.00.2002 miniature, modular mechanical standard specifications.

6. The system according to claim 1, wherein said at least one MRI device is in indirect connection with the drilling mud recycling line via at least one bypass of said drilling mud recycling line.

7. The integrated system according to claim 1, wherein said at least one MRI device is in connection with more than one drilling mud recycling line.

8. A method for analyzing and treating a drilling mud in a drilling mud recycling process, comprising:
providing a system comprising a drilling mud recycling line comprising drilling mud recycling equipment configured to perform a process of recycling drilling mud;
incorporating an MRI device into said drilling mud recycling line;
imaging at least a portion of said drilling mud by means of said MRI device, thereby obtaining at least one image;
analyzing said at least one image to derive at least one value of at least one rheological parameter of said drilling mud;
generating at least two radial pressure profiles of said drilling mud; and
controlling at least one step of said drilling mud recycling process according to said at least one value of said at least one rheological parameter.

9. The method according to claim 8, wherein said at least one step of said drilling mud recycling process is selected from the group consisting of adding ingredients to said drilling mud, mixing, shaking, rotating, tumbling, aerating, heating, cooling, holding at a fixed temperature, emulsifying, adding water or water immiscible solutions, grinding, grounding, milling, shredding, pulverizing, cutting, filtering, reducing particle size, de-emulsifying, kneading, decanting, settling, distilling, decentering, vacuuming, and any combination thereof.

10. The method according to claim 8, wherein said step of analyzing comprises:
generating at least one radial velocity profile of said drilling mud; and,
deriving said at least one rheological parameter from said at least one radial velocity profile and at least two radial pressure profiles.

11. The method according to claim 8, wherein said at least one rheological parameter is selected from the group consisting of:
radial shear stress parameter $\sigma(r)$;
radial shear rate parameter $\gamma(r)$; and,
stress parameters k and n in the power law equation $\delta(r)=k[\gamma(r)]^n$.

12. The method according to claim 11, additionally comprising:
determining a quality parameter Q, $Q=\sqrt{k^2+n^2}$; and,
comparing said quality parameter Q to a standard quality parameter $Q_s$ of a standardized sample of a drilling mud, $Q_s=\sqrt{k_s^2+n_s^2}$, where stress parameters ks and ns are given by a power law equation $\sigma_s(r)=k_s[\gamma_s(r)]^{ns}$ and $\sigma s(r)$ and $\gamma s(r)$ are the radial shear stress and the radial shear rate, respectively, of said standardized sample.

13. The method according to claim 12, additionally comprising:
generating a quality test parameter $O_T=|O_S-Q|$;
if said quality test parameter is smaller than a predetermined value:
inputting a further batch of said drilling mud into said drilling mud recycling line;
if said quality test parameter is larger than said predetermined value:
instructing said drilling mud recycling equipment to perform at least one step selected from the group consisting of adding ingredients and raw materials, mixing, shaking, rotating, tumbling, aerating, heating, cooling, holding at a fixed temperature, emulsifying, adding water or water immiscible solutions, grinding, grounding, milling, shredding, pulverizing, cutting, filtering, reducing particle size, de-emulsifying, kneading, decanting, settling, distilling, decentering, vacuuming, and any combination thereof, said step of instructing performed by said processor.

14. The method according to claim 13, wherein said predetermined value equals one standard deviation of said standard quality parameter.

15. The method according to claim 8, wherein at least one of the following is true:

said drilling mud recycling equipment complies with a NeSSI specification; and, at least a part of said drilling mud recycling equipment complies with ANSI/ISA SP76.00.2002 miniature, modular mechanical standard specifications.

16. The method according to claim 8, wherein said MRI device is in indirect connection with the drilling mud recycling line via at least one bypass of said drilling mud recycling line.

17. The method according to claim 8, wherein said MRI device is in connection with more than one drilling mud recycling line.

18. The method according to claim 8, wherein said step of imaging comprises:

imaging said drilling mud before and after reusing said drilling mud in a drilling hole.

19. The method according to claim 8, further comprising:

providing said system with one or more non-resonance magnetic analysis means; and, analyzing said drilling mud by said non-resonance magnetic analysis means to obtain at least one parameter selected from the group consisting of flow rate, density, water cut (water ratio), viscosity, particle size, and salinity.

* * * * *